United States Patent [19]
Gratale et al.

[11] Patent Number: 6,143,887
[45] Date of Patent: Nov. 7, 2000

[54] PROCESS FOR THE STEREOSELECTIVE SYNTHESIS OF 16-SUBSTITUTED-4-AZA-ANDROSTANONES

[75] Inventors: Dominick F. Gratale, Edison; Richard L. Tolman, Warren; Soumya P. Sahoo, Old Bridge, all of N.J.

[73] Assignee: Merck & Co., Inc., Rahway, N.J.

[21] Appl. No.: 09/309,833

[22] Filed: May 11, 1999

Related U.S. Application Data

[60] Provisional application No. 60/085,449, May 14, 1998.

[51] Int. Cl.⁷ ...................... C07D 401/12; C07D 403/12; C07D 221/18; C07D 241/08; C07D 253/06
[52] U.S. Cl. .......................... 544/182; 544/238; 544/316; 544/408; 546/78
[58] Field of Search ...................... 544/182, 238, 544/316, 408; 546/78

[56] References Cited

U.S. PATENT DOCUMENTS

| | | | |
|---|---|---|---|
| 5,455,348 | 10/1995 | Austel et al. | 544/238 |
| 5,719,158 | 2/1998 | Durette et al. | 544/408 |
| 5,739,137 | 4/1998 | Durette et al. | 514/256 |
| 5,910,497 | 6/1999 | Durette et al. | 514/253 |

FOREIGN PATENT DOCUMENTS

| | | |
|---|---|---|
| WO 95/11254 | 4/1995 | WIPO . |
| WO 96/03129 | 2/1996 | WIPO . |
| WO 98/00137 | 1/1998 | WIPO . |
| WO 99/32507 | 12/1998 | WIPO . |

OTHER PUBLICATIONS

Zhao et al., Tet. Letters, vol. 38, No. 31 (1997), pp. 5437–5440, "Syntheses of alkylated malonates in a traceless linker derived soluble polymer support".

*Primary Examiner*—Alan L. Rotman
*Attorney, Agent, or Firm*—Catherine D. Fitch; Melvin Winokur

[57] ABSTRACT

The novel process of the present invention involves the stereoselective synthesis of certain 16β-substituted 4-aza-5α-androstan-3-ones and the useful intermediates obtained therein.

8 Claims, No Drawings

PROCESS FOR THE STEREOSELECTIVE SYNTHESIS OF 16-SUBSTITUTED-4-AZA-ANDROSTANONES

CROSS REFERENCE TO RELATED APPLICATIONS

The present application claims priority of U.S. provisional application Ser. No. 60/085,449, filed May 14, 1998.

BACKGROUND OF THE INVENTION

Certain undesirable physiological manifestations, such as acne vulgaris, seborrhea, female hirsutism, androgenic alopecia which includes female and male pattern baldness, and benign prostatic hyperplasia, are the result of hyperandrogenic stimulation caused by an excessive accumulation of testosterone ("T") or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neri, et al., *Endocrinol.* 1972, 91 (2). However, these products, though devoid of hormonal effects, compete with all natural androgens for receptor sites, and hence have a tendency to feminize a male host or the male fetus of a female host and/or initiate feed-back effects which would cause hyperstimulation of the testes.

The principal mediator of androgenic activity in some target organs, e.g. the prostate, is 5α-dihydrotestosterone ("DHT"), formed locally in the target organ by the action of testosterone-5α-reductase (or simply 5α-reductase). Inhibitors 5α-reductase will serve to prevent or lessen symptoms of hyperandrogenic stimulation in these organs. See especially U.S. Pat. Nos. 4,377,584, issued Mar. 22, 1983, and 4,760,071, issued Jul. 26, 1988, both assigned to Merck & Co., Inc. It is now known that a second 5α-reductase isozyme exists, which interacts with skin tissues, especially in scalp tissues. See, e.g., G. Harris, et al., *Proc. Natl. Acad. Sci. USA*, Vol. 89, pp. 10787–10791 (November 1992). The isozyme that principally interacts in skin tissues is conventionally designated as 5α-reductase 1 (or 5α-reductase type 1), while the isozyme that principally interacts within the prostatic tissues is designated as 5α-reductase 2 (or 5α-reductase type 2).

U.S. Pat. No. 5,237,064 describes a process for producing 7β-substituted 5α-androstan-3-ones. U.S. Pat. No. 5,470,976 describes the stereoselective hydrogenation of the delta-5 double bond of a 17-substituted azasterold. U.S. Pat. Nos. 5,120,847 and 5,021,575 relate to the insertion of a double bond at the 1,2 position of a 4-azasteroid.

The instant invention provides an improved process for the synthesis of 16α- or β-substituted 4-aza-5α-androst-1-en-3-ones and 5α-androstan-3-ones. 16-stubstituted 4-aza-5α-androstan-3-ones are described in U.S. Pat. No. 5,719,158. The present invention provides a process of formation of a methylsulfonate and nucleophilic displacement thereof that proceeds without side-reaction with the ene-lactam functionality. Also provided by the present invention are intermediates useful in the present process.

SUMMARY OF THE INVENTION

The novel process of this invention involves the stereoselective synthesis of certain 16-substituted 4-aza-5α-androst-1-en-3-ones, and the useful intermediates obtained therein. These novel intermediates and this novel process can be exemplified in the following embodiment.

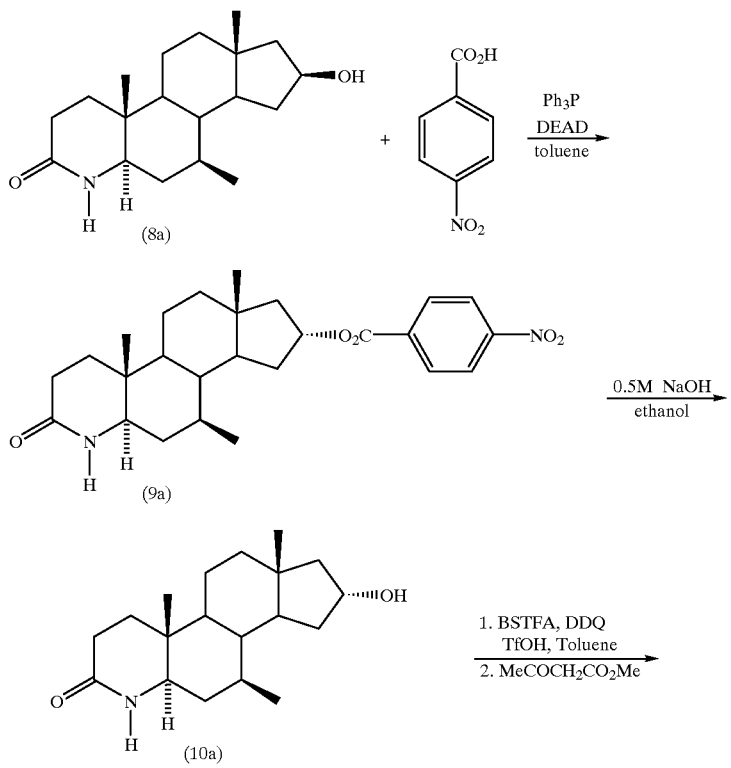

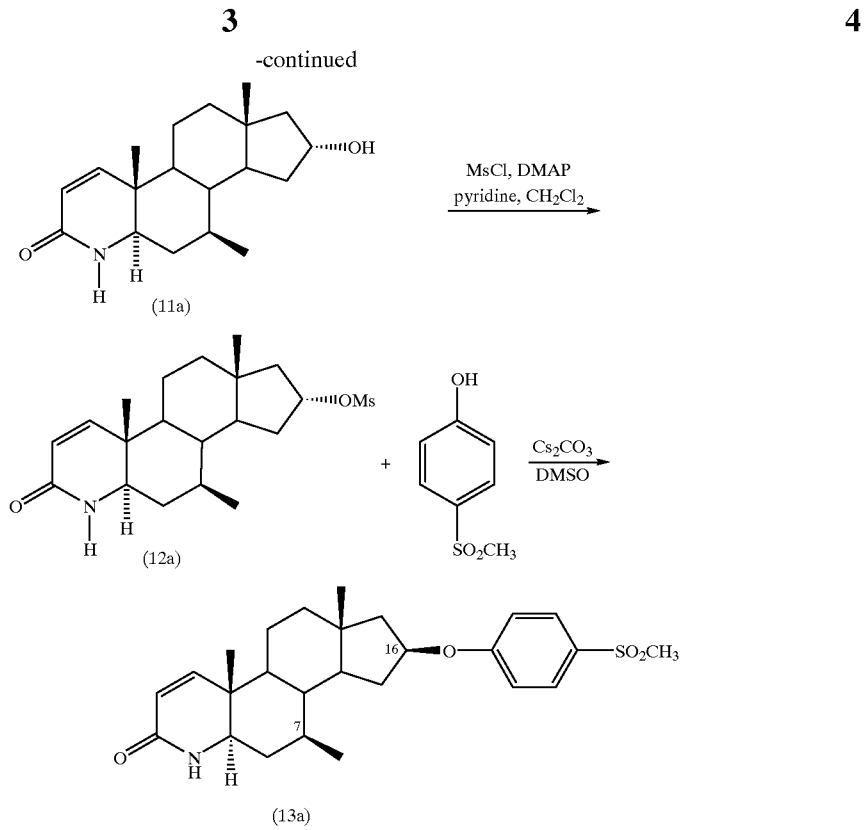

The products of the present process are useful as a inhibitors of 5α-reductase, particularly 5α-reductase type 1. 5α-reductase inhibitors are useful in the treatment of hyperandrogenic disorders such as benign prostatic hyperplasia, acne vulgaris, seborrhea, female hirsutism, androgenic alopecia (androgenetic alopecia), including male pattern baldness, and the prevention and treatment of prostatic carcinoma.

DETAILED DESCRIPTION OF THE INVENTION

A general procedure for the process of the present invention is shown below in Schemes 1 and 2:

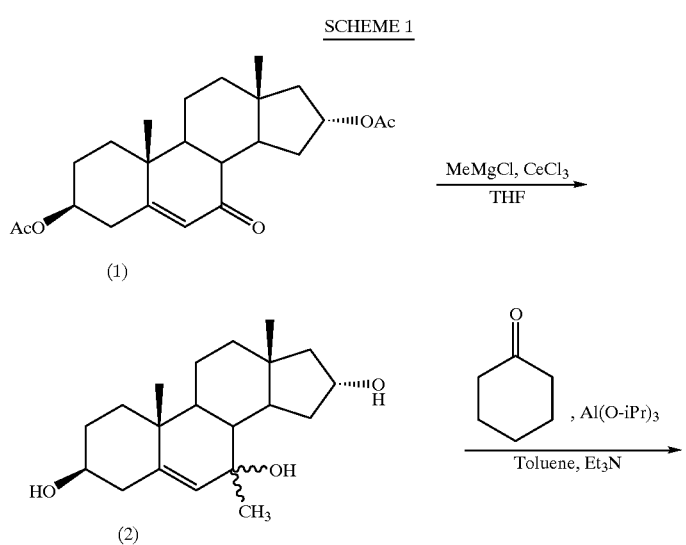

-continued
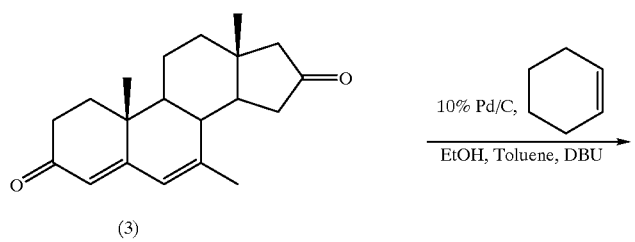
(3)
10% Pd/C,
———————→
EtOH, Toluene, DBU
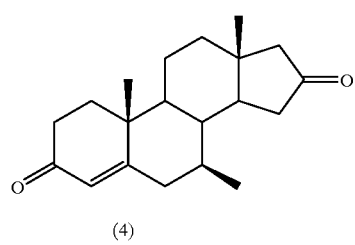
(4)
KMnO₄
———————→
NaIO₄/t-BuOH/H₂O
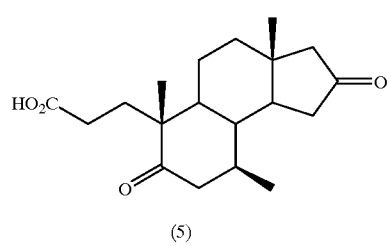
(5)
NH₄OAc
————→
AcOH
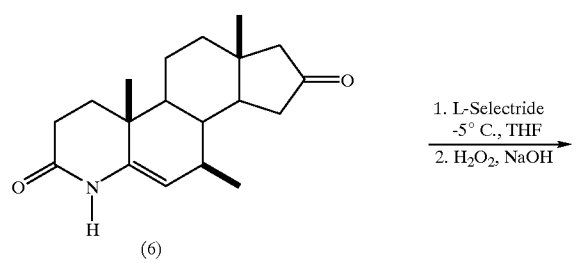
(6)
1. L-Selectride
   -5° C., THF
———————→
2. H₂O₂, NaOH
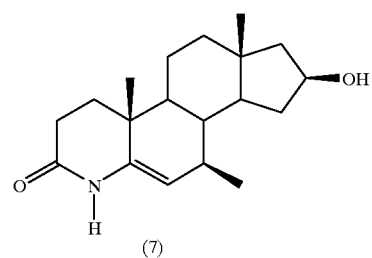
(7)
1. H₂, IPA, 50° C.
———————→
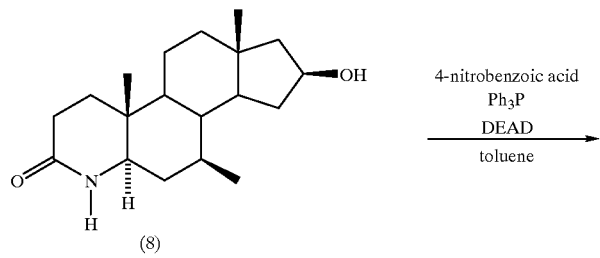
(8)
4-nitrobenzoic acid
Ph₃P
DEAD
————→
toluene

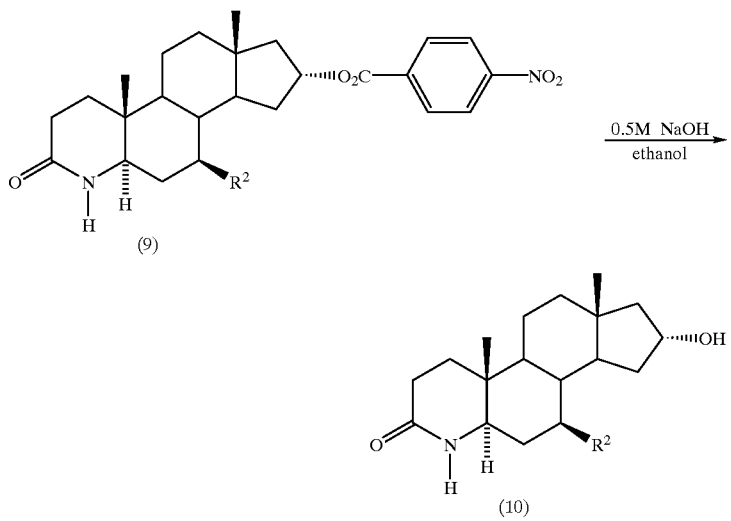

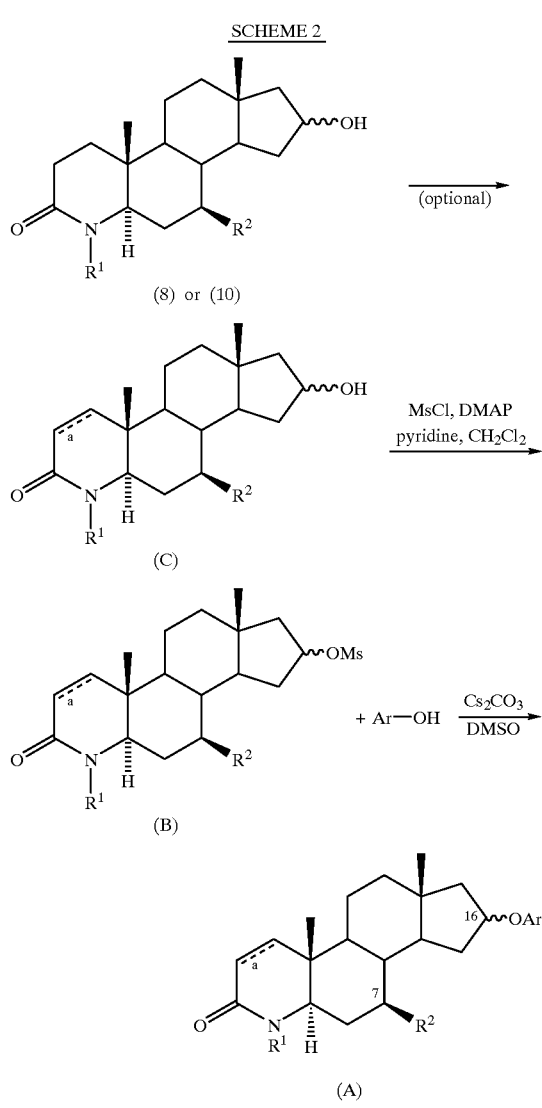

wherein:

the dotted line "a" is a single bond or a double bond;

$R^1$ is H or $CH_3$;

$R^2$ is H or $CH_3$;

Ar is:

unsubstituted or mono- or di-substituted phenyl, naphthyl, or 5 or 6 membered heteroaromatic ring containing at least one member selected from the group consisting of: one ring oxygen atom, one ring sulfur atom, 1–4 ring nitrogen atoms, or combinations thereof; in which the heteroaromatic ring can also be fused with one benzo or heteroaromatic ring.

Alternatively, the β-lactam alcohol (8) may be treated with methanesulfonylchloride to form the β-mesylate (B) and the α-aryloxy product (A).

The squiggly bond at the 16-position in structures A, B, and C indicates either R or S stereochemistry at the 16-position. If C has 16(R)-stereochemistry, B is (R) a Ld A is (S); conversely, if C has 16(S)-stereochemistry, B is (S) and A is (R).

Furthermore, as is apparent to one of ordinary skill in the art, the process of the present invention is also useful with compounds having 17- or 15-position substitution in addition to the 16-substituent.

When Ar is heteroaryl, the heteroaryl ring may be attached within structural formula I or substituted on any carbon atom in the ring which results in the creation of a stable structure.

The substituents on the aryl and heteroaryl groups named above are independently selected from:

i) halo; hydroxy; cyano; nitro; mono-, di- or trihalomeihyl; mono-, di- or trihalomethoxy; $C_{2-6}$ alkenyl; $C_{3-6}$ cycloalkyl; formyl; hydrosulfonyl; carboxy; ureido;

ii) $C_{1-6}$ alkyl; hydroxy $C_{1-6}$ alkyl; $C_{1-6}$ alkyloxy; $C_{1-6}$ alkyioxy $C_{1-6}$alkyl; $C_{1-6}$ alkylcarbonyl; $C_{1-6}$ alkylsulfonyl; $C_{1-6}$ alkylthio; $C_{1-6}$ alkylsulfinyl; $C_{1-6}$ alkylsulfonamido; $C_{1-6}$ alkylarylsulfonamido; $C_{1-6}$ alkyloxycarbonyl; $C_{1-6}$ alkyloxycarbonyl $C_{1-6}$alkyl; $R_bR_cN$—C(O)-$C_{1-6}$alkyl; $C_{1-6}$ alkanoylamino $C_{1-6}$ alkyl; aroylamino $C_{1-6}$ alkyl; wherein the $C_{1-6}$ alkyl moiety is unsubstituted or substituted with 1–3 of: halo; $C_{1-4}$alkoxy; or trifluoromethyl;

iii) aryl; aryloxy; arylcarbonyl; arylthio; arylsulfonyl; arylsulfinyl; arylsulfonamido; aryloxycarbonyl;

wherein the aryl moiety is unsubstituted or substituted with 1–3 of: halo; $C_{1-4}$alkyl; $C_{1-4}$alkoxy; or trifluoromethyl;

iv) —C(O)NR$_b$R$_c$; —O—C(O)—NR$_b$R$_c$; —N(R$_b$)—C(O)—R$_c$; —NR$_b$R$_c$; R$_b$—C(O)—N(R$_c$)—; where R$_b$ and R$_c$ R$_b$ and R$_c$ are independently H, $C_{1-6}$ alkyl, aryl, or aryl $C_{1-6}$alkyl; wherein the alkyl moiety is unsubstituted or substituted with 1–3 of: halo; $C_{1-4}$alkoxy; or trifluoromethyl; and the aryl moiety can be substituted with 1–3 of: halo; $C_{1-4}$alkyl; $C_{1-4}$ alkoxy; or trifluoromethyl; and —N(R$_b$)—C(O)—OR$_g$, wherein R$_g$ is $C_{1-6}$alkyl or aryl, in which the alkyl moiety is unsubstituted or substituted with 1–3 of: halo; $C_{1-4}$alkoxy; or trifluoromethyl, and the aryl moiety is unsubstituted or substituted with 1–3 of: halo; $C_{1-4}$alkyl; $C_{1-4}$ alkoxy, or trifluoromethyl; —N(R$_b$)—C(O) NR$_c$R$_d$, wherein R$_d$ is selected from H, $C_{1-6}$ alkyl, and aryl; in which said $C_{1-6}$alkyl and aryl is unsubstituted or substituted as described above in (f) for R$_b$ and R$_c$;

iv) a heterocyclic group, wherein the heterocyclic ring can be fused with a benzo ring, and wherein said heterocyclic ring is unsubstituted or substituted with one to three substituents, as defined above for i), ii), and iii).

Preferably, Ar is sele(cted from: unsubstituted or mono- or di-substituted phenyl, naphthyl, pyridyl, furyl, pyrrolyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl, and benzoxazolyl.

In another embodiment, Ar is selected from: unsubstituted or mono- or di-substituted phenyl, naphthyl, pyridyl, pyrrolyl, pyrazinyl, pyrimidyl, and oxazolyl.

In still another embodiment, Ar is monosubstituted phenyl.

Preferably, the aryl and heteroaryl substituents are selected from:

v) halo; cyano; nitro; trihalomethyl; trihalomethoxy; $C_{1-6}$ alkyl; aryl; $C_{1-6}$ alkylsulfonyl; $C_{1-6}$ alkylarylsulfonamino;

vi) —NR$_b$R$_c$; R$_b$—C(O)—N(R$_c$)—; wherein R$_b$ and R$_c$ are independently H, $C_{1-6}$ alkyl, aryl, or aryl $C_{1-6}$alkyl; wherein the alkyl moiety is unsubstituted or substituted with 1–3 of: halo; $C_{1-4}$alkoxy; or trifluoromethyl; and the aryl moiety is unsubstituted or substituted with 1–3 of: halo; $C_{1-4}$alkyl; $C_{1-4}$ alkoxy; or trifluoromethyl;

vii) a heterocyclic group, which is a 5 membered aromatic ring, containing one ring nitrogen atom, or one ring oxygen and one ring nitrogen atom.

Combinations of substituents and/or variables are permissible only if such combinations result in stable compounds.

As used herein "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonyl, decyl, iso-propyl (i-Pr), iso-butyl (i-Bu), tert-butyl (t-Bu), sec-butyl (s-Bu), iso-pentyl, and the like. "Alkyloxy" (or "alkoxy") represents an alkyl group having the indicated number of carbon atoms attached through an oxygen bridge, e.g., methoxy, ethoxy, propyloxy, and the like. "Alkenyl" is intended to include hydrocarbon groups of either a straight or branched configuration with one or more carbon-carbon double bonds which may occur in any stable point along the chain, such as ethenyl, propenyl or allyl, butenyl, pentenyl, and the like. Included in this invention are all E, Z diasteriomers.

Whenever the terms "alkyl", "alkenyl", "alkyloxy (or alkoxy)", "aryl" or "heteroaryl", or one of their prefix roots, appear in a name of a substituent in formula I, (e.g. aralkoxyaryloxy) they shall have the same definitions as these described above for "alkyl", "alkenyl", "alkyloxy (or alkoxy)", "aryl" and "heteroaryl", respectively. Designated numbers of carbon atoms (e.g. $C_{1-10}$) shall refer independently to the number of carbon atoms in an alkyl or alkenyl moiety or to the alkyl or alkenyl portion of a larger substituent in which alkyl or alkenyl appears as its prefix root.

The process and intermediates of the present invention can be performed and prepared readily according to the following reaction Schemes and Examples or modifications thereof using readily available starting materials reagents and conventional synthesis procedures. In these reactions, it is also possible to make use of variants which are themselves known to those of ordinary skill in this art, but are not mentioned in greater detail. Some abbreviations used herein are as follows: Ph is phenyl; Ac is an acyl group; t-Bu is tert-butyl; Et is ethyl; Me is methyl; i-Am is iso-amyl; EtOAc is ethyl acetate; Ms is mesyl or methanesulfonyl.

The starting material for the process is produced according to the procedures in Miller et al., Tetrahedron Letters 37(20) 3429–3432 (1996) and those in PCT publication WO 95/32215, and is generally known and available in the art.

As shown in Scheme 3, addition of methyl magnesium chloride to the 7-keto-3,16 bis acetate starting material (1) cleaves the 3 and 16 acetates with concurrent addition to the 7-ketone to produce (2). Anhydrous cerium trichloride, in the proper needle form, was added to the Grignard before addition to the 7-ketone and improved the yield of the reaction by >15%. The triol (2) can be carried on to the next step without purification, or it may be isolated Oxidation of the triol (2) to the dienedione (3) was carried out under Oppenauer conditions with 2-butanone, aluminum isopropoxide, and triethylamine. Concurrent hydrolysis of the aluminum salts and elimination of the 7-OH occurred upon aging with concentrated HCl. Butanone dimers can be removed from the reaction mixture by a water distillation before carrying on to the next step, or the dienedione (3) may be isolated.

A chemo- and stereoselective reduction of the dienone (3) to the 7-β methyl enone (4) was achieved under transfer hydrogenation conditions using 10% Pd/C and cyclohexene as the hydrogen donor. Careful front run of the reaction and frequent monitoring ensured little overreduction and a high yield of enone.

The oxidative cleavage of the enone (4) to the seco acid (5) was carried using sodium periodate and catalytic potassium permangante with sodium carbonate.

Introduction of the nitrogen atom into the A ring occurs in refluxing acetic acid with ammoniuml acetate. BHT was added as a radical inhibitor to prevent decomposition of enelactam ketone (6). Procedures are well known in the art for introducing an N-methyl at this position. See, e.g. U.S. Pat. No. 5,719,158.

Chemo- and stereoseletive reduction of the crude enelactam ketone (6) was carried out with L-Selectride™ at −5° C. After an oxidative workup to convert the trialkylboron by-products to boric acid, the enelactam alcohol (7) is crystallized from acetonitrile. Running this reaction under more dilute conditions and reducing the level of toluene improves yield.

Hydrogenation of the enelactam alcohol (7) is critical because enelactam left behind does not crystallize away from the NH lactam β-alcohol (8) and impacts on the purity of the final product.

Similarly, the 7-unsubstituted derivative of the NH lactam β-alcohol (8) may be produced by nmeans known to those of ordinary skill in the art.

Scheme 4 illustrates conversion of the 16β-alcohol (8) to the 16α-alcohol (10) proceeds through the 4-nitrophenyl ester (9) which is not purified.

Introduction of the delta-1 double bond to form the 16α-hydroxy-4-aza-5α-androst-1-en-3-one derivative (11) proceeds through the process described in U.S. Pat. No. 5,084,574 by reacting with a silylating agent in the present of a quinone. Alternatively, other known processes for insertion of the delta-1-double bond may be employed, see e.g., U.S. Pat. Nos. 5,091,534; 5,120,847; and 5,021,575.

Alternatively, the 16α-alcohol (10) may be treated with methane sulfonylchloride in order to produce the 1,2-saturated derivative; skipping the step of double bond formation.

Formation of the 16α-methyl sulfonate (12) is optimally carried out in a polar aprotic solvent such as methylene chloride in the presence of an organic base such as pyridine by reaction with methane sulfonylchloride. Optionally, dimetitylaminopyridine (DMAP) may be added to the reaction mixture as a catalyst.

The 16α-methyl sulfonate is converted into the desired 16β-aryloxy product (13) by reaction with the appropriately substituted hydroxyaryl derivative and cesium carbonate in a polar aprotic solvent such as DMSO (dimethylsulfoxide), DMF (N,N-dimethylformamide), nitromethane, dioxane, THF (tetraliydrofuran), and acetonitrile, preferably DMSO.

Alternatively, as shown in Scheme 5, the 16β-methyl sulfonate may be formed from the 16β-alcohol (8), either by first introducing the delta-1 double bond according to the procedures described above to produce (14), followed by reacting the delta-1-16β-alcohol (14) with mesyl chloride in a polar aprotic solvent in the presence of an organic base as described above to form the delta-1-16β-methyl sulfonate (15). The lactam β-alcohol (8) may also be directly treated with mesyl chloride to form the corresponding 16β-methyl sulfonate derivative with an saturated A-ring (17). The 16β-mesylate (15, 17) is then converted to the desired 16α-aryloxy product (16, 18) by reaction with the appropriately substituted hydroxyaryl derivative and cesium carbonate in a polar aprotic solvent such as DMSO.

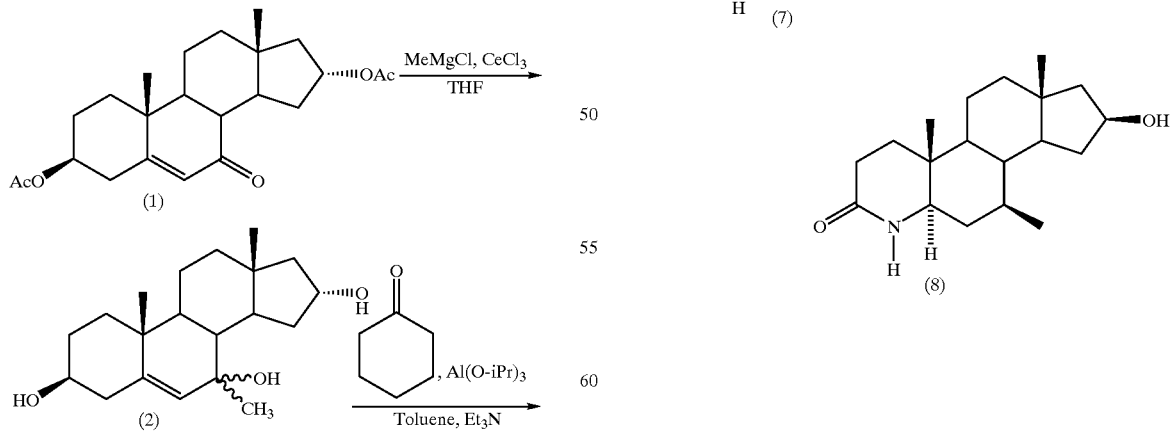

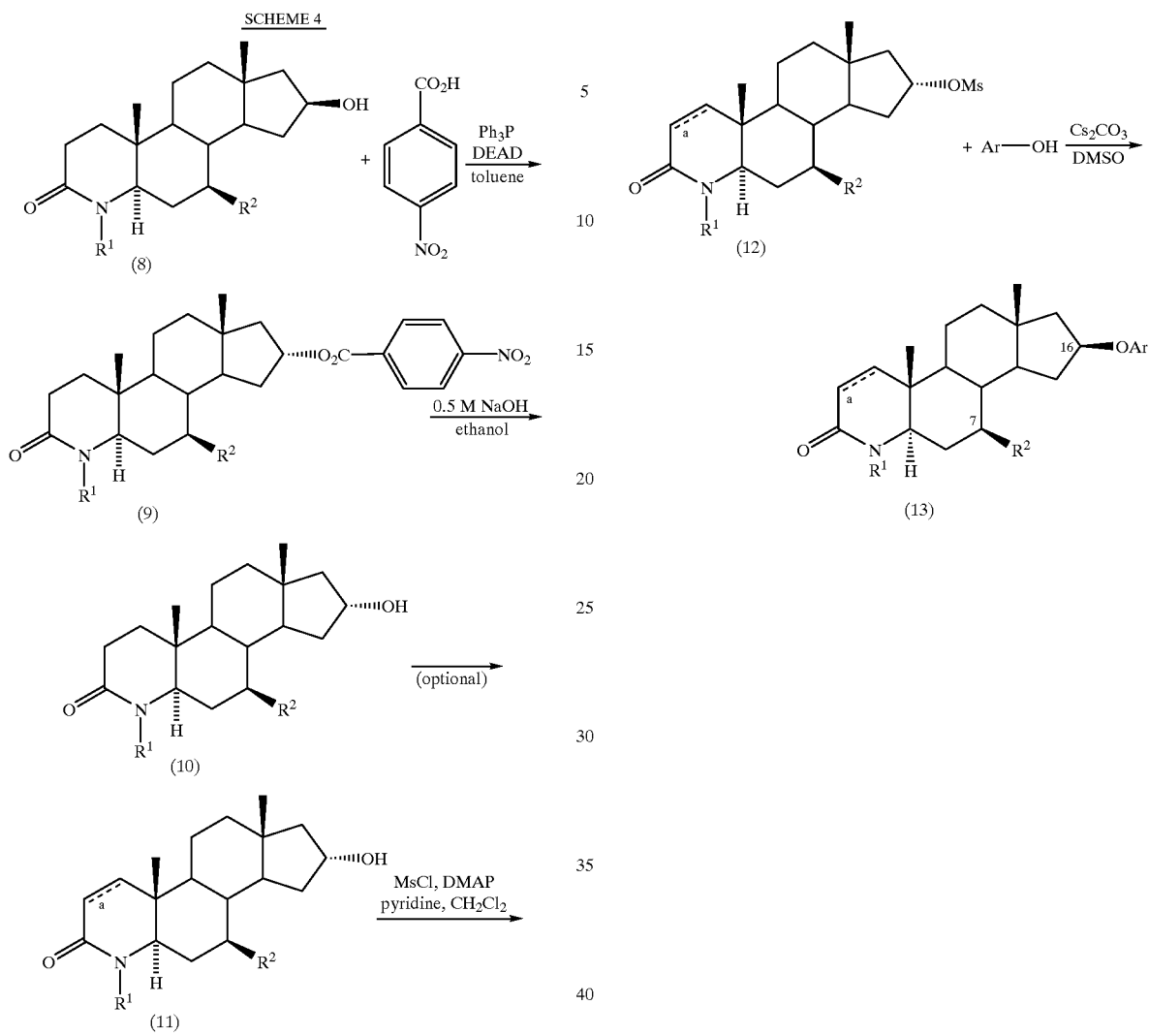
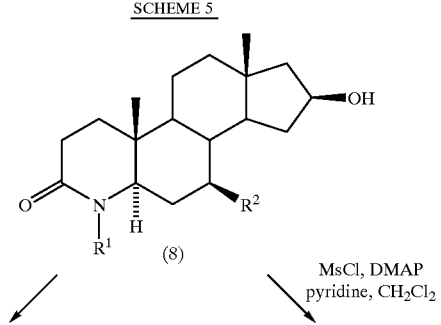

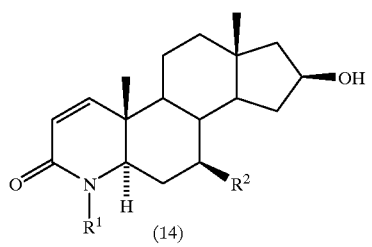

(14)

| MsCl, DMAP
| pyridine, CH$_2$Cl$_2$
↓

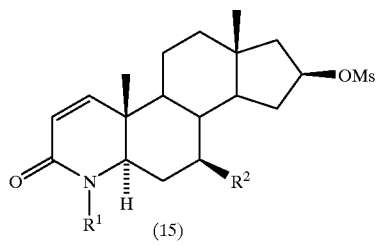

(15)

| ArOH
| Cs$_2$CO$_3$
| DMSO
↓

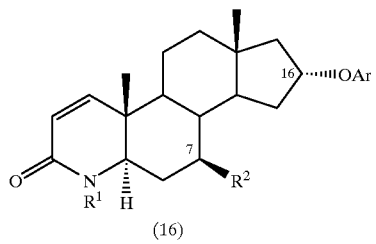

(16)

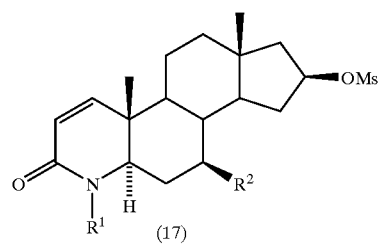

(17)

| ArOH
| Cs$_2$CO$_3$
| DMSO
↓

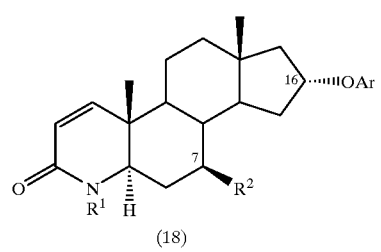

(18)

In addition to the 16-methyl sulfonate intermediates (12), (15), (17), employed herein, any good sulfonate leaving-group may be employed, e.g., 2,4,6,-triisopropyl sulfonate, toluene sulfonate, etc.

The following examples are provided to further illustrate details for the preparation of the compound of the present invention. The examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds. All temperatures are in degrees Celsius unless noted otherwise.

Abbreviations: ACN is a acetonitrile; BHT is 2,6-t-butyl-4-methylphenol; ca is circa; DBU is (1,8-diazabicyclo[5.4.0]undec-7-ene; IPA is isopropyl alcohol; L-Selectride® is lithium tri-sec-butylborohydride; MEK is methyl ethyl ketone; Ms or mesyl is methane sulfonyl; NMP is 1-methyl-2-pyrrolidinone; PDA is photo diode array; THF is tetrahydrofuran; TMEDA is N,N,N',N'-Tetramethylethylenediamine; TMSCl is chlorotrimethylsilane.

EXAMPLE 1

Preparation of 3,6,16-Triol (2)

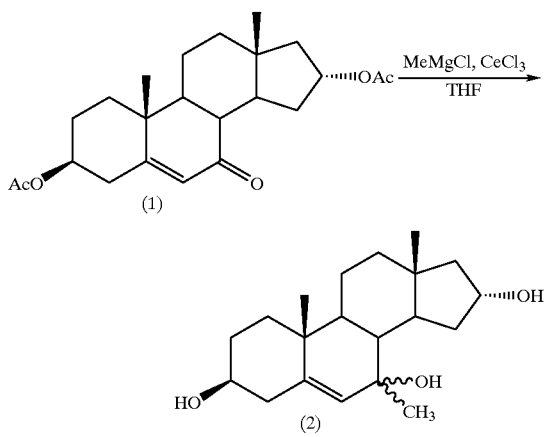

Cerium chloride (3.96 kg) was charged as a solid to the reaction vessel. THF (35 kg) was charged using vacuum, then water (20 mL) was added via the charge port and the mixture aged at 35° C. for 1 hr. A sample was taken and examined by microscopy to ensure that conversion to the required crystal form had occurred.

(Amorphous cerium chloride stirred in THF converts to a fine rod-like crystalline form. This crystalline form is necessary to obtain the stereo-selectivity in the Grignard reaction. Previous experience had shown that the water content of the THF/cerium chloride should be less than 1000 ppm in order to get the required crystal form. Wetter slurries were found to irreversibly form another crystal form that did not exhibit the same specificity in the Grignard reaction. However, the THF used in this instance was extremely dry (<50 ppm) and stirring the amorphous cerium chloride in it did not produce the required conversion and the solid remained amorphous. It was demonstrated that a small amount of water is necessary for the conversion to take place, and water was added to the batch to give a total water content of ca 500 ppm.)

After cooling the batch to 25° C., 3M methyl magnesium chloride in THF (80.46 kg) was added to the vessel. The mixture was cooled to 0–5° C. and aged for 30 minutes. The 7-ketone starting material (1) (9.2 kg) was slurried in THF (50 L) and added to the Grignard reagent slurry over 75 minutes, maintaining a temperature of <20° C.

The batch was sampled and reaction completion confirmed by HPLC: <0.1 A % (1) detected. The Grignard reaction mixture was slowly added to a quenching solution formed by the addition of toluene (70 kg) to a solution of water (146 L) and solid citric acid (43.9 kg). Care was made to maintain the temperature at <20° C. The reaction vessel and transfer lines were rinsed with PHF (10 kg).

The mixture was stirred for 15 minutes then settled for 30 minutes. Both phases were cut to drums and the aqueous layer returned to was back extracted with 39 kg of ethyl acetate (agitated for 10 mins, settled for 30 mins). The aqueous layer was cut to waste drums and the THF batch layer was combined with the ethyl acetate layer. 20% sodium carbonate solution (49.2 kg) was added to the stirred solution over 15 minutes then the mixture settled for 30 minutes and the aqueous phase cut to waste.

The batch layer was washed with 51.5 kg of 20% sodium chloride solution (agitated for 10 mins, settled for 30 minutes) and the aqueous phase cut to waste. Triethylamine (4.8 kg) was added and the solution concentrated in vacuo to ca 100 L. Toluene was added and distillation continued, until the level of THF/ethyl acetate had dropped to <0.5 vol % by GC. The final volume was made up to 275 L, with toluene and the slurry held was used in Example 2.

HPLC Conditions:

| | |
|---|---|
| Column | YMC J-Sphere ODS H80 250 × 4.6 mm I.D. |
| Eluent A | ACN |
| Eluent B | Unbuffered water |
| Gradient | 30% A to 80% A in 25 min; hold for 5 min |
| Inj vol | 20 μl |
| Detection | UV at 200 nm |
| Flow | 1.5 ml/min |
| Column temp | 35° C. |
| Sample preparation | 100x dilution with acetonitrile; waste aq layers diluted 50x |

| Compound | Retention Times | Response Factor(area counts/wt) |
|---|---|---|
| Triols | 4.6, 6.4 | 0.71 |
| 7-ketone | 14.6 | 1 |
| Toluene | 16.4 | |
| BHT | 29.5 | |

GC conditions

| | |
|---|---|
| Column coating | Chrompack plot fused silica 25 m × 0.53 mm poraplot Q |
| Oven temperature | 250° C. Isothermal |

-continued

| | |
|---|---|
| Inj temp | 275° C. |
| Det temp | 275° C. |
| Sample preparation | 40x dilution with MeOH |

| Compound | Retention | Relative Response Factor |
|---|---|---|
| MeOH | 2.0 min | |
| THF/EtOAc | 2.8, 3.2 min | 1 |
| Toluene | 4.5 min | 1.5 |

EXAMPLE 2

Preparation of Diene-Dione (3)

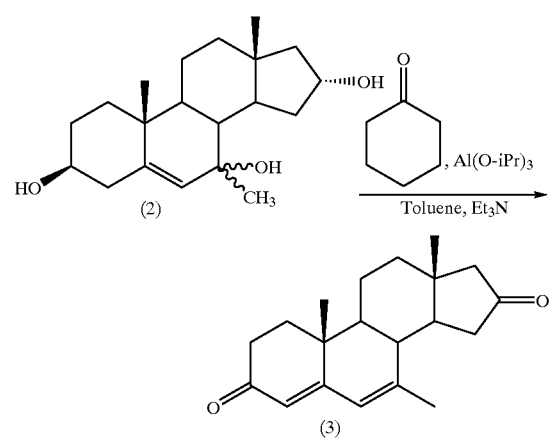

To a slurry of triol in toluene (7.59 kg in 275 L) was added triethylamine (3.8 kg) and aluminium isopropoxide (10 kg) followed by 2-butanone (100 kg). The mixture was heated at reflux for 6 hrs, cooled slightly, a sample was taken, and reaction completion confirmed by HPLC (<5 A % 16-OH's dienone relative to 16-keto-diene-dione). The batch was cooled to 20° C., then allowed to stand overnight.

A mixture of water (62.5 L) and 12 N hydrochloric acid (73.7 kg) was transferred to the reaction mixture. The reaction mixture was heated to 58–60° C. and aged for 4 hrs. A sample was taken and the disappearance of 7-OH enone intermediate confirmed by HPLC. The batch was cooled to 20° C., allowed to settle for 15 mins and the aqueous phase cut to waste.

2.5% sodium bicarbonate solution (100 L) was added to the toluene layer, stirred for 15 mins, settled for 30 mins and the aqueous phase cut to waste. This procedure was repeated with 100 L of water.

The organic phases from the two batches prepared as described above were combined and concentrated in vacuo to a volume of 100 L. Water was fed in under vacuum then distillation continued at atmospheric pressure until the level of 2-butanone dimers in the batch had dropped to <3 A % relative to diene-dione; a total of 70 L of water was distilled. Toluene (100 L) was added to the residue, the mixture agitated for 5 mins then settled for 15 mins. The organic layer was saved. The aqueous phase returned was extracted with toluene (40 L). The organic layers were combined and concentrated in vacuo to a final volume of ca 60 L. The solution was held for Example 3.

| HPLC Conditions | |
|---|---|
| Column | YMC J-Sphere ODS H80 250 × 4.6 mm I.D. |
| Eluent A | ACN |
| Eluent B | Unbuffered water |
| Gradient | 30% A to 80% A in 25 min; hold for 5 min |
| Flow | 1.5 ml/min |
| Inj vol | 20 µl |
| Detection | UV at 200 nm for triols, 240 nm for 7-OH enone and MEK by-product removal, 290 nm for dienone assays |
| Column temp | 35° C. |
| Sample preparation | 100x dilution with acetonitrile; waste aq layers diluted 25–50x |

| Compound | Retention Times | λ |
|---|---|---|
| Triols | 4.6, 6.4 | 200 nm |
| 7-OH enone | 6.6 | 240 nm |
| Dienedione | 13.1 | 290 nm |
| Toluene | 16.4 | 200 nm |
| BHT | 29.5 | 200 nm |

EXAMPLE 3
Preparation of Enone (4)

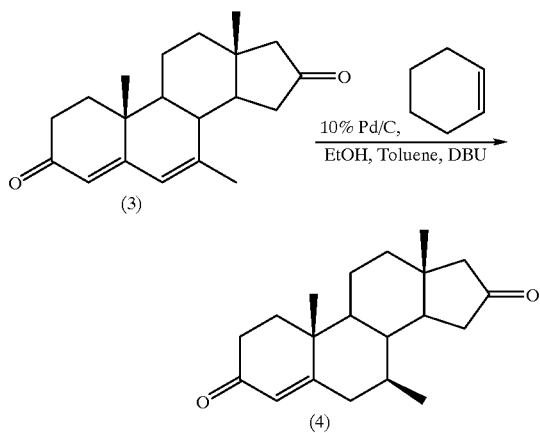

Diene-dione (3) (12.9 kg) was converted to enone (4) (11.69 assay kg, 90.0% yield) in one batch. The enone was not isolated but carried through for use in Example 4 as a solution in t-butanol.

To the reaction vessel was added 10% Pd/C (5.32 kg, 51.5% water wet), followed by the toluene solution of diene-dione obtained as a product of Example 2, (12.9 kg in 70 L), ethanol (38.1 L), and cyclohexene (64.9 L). The mixture was agitated and DBU (1.28 kg) was added.

A sample was taken and the mixture warmed to reflux. The reaction was sampled periodically and heating continued (6 hrs) until the diene-dione level, measured by HPLC fell below 1.0 mg/ml.

(As benzene is produced as a by-product of the reaction, care was taken to use local extraction when sampling.)

After cooling to 25° C., the batch was filtered through a 45 cm plate filter set with a polypropylene cloth, card, and Solka Floc diatomaceous earth (1.5 kg).

The filter became blocked after about 50% of the slurry had passed through and had to be dismantled and reset.

The vessel, lines and filter pad were rinsed with toluene (20 L) and the combined filtrates allowed to stand overnight. 1 N hydrochloric acid (44 L) was added to the filtrate. The mixture was agitated for 5 mins, settled for 15 mins and the lower aqueous phase cut to waste. This wash procedure was repeated with 5% sodium chloride solution (42 L).

The organic phase was concentrated in vacuo to ca 50 L then transferred to a reaction vessel via a 0.5µ cotton cartridge filter and distillation continued to ca 22 L. The solvent was switched to t-butanol. t-Butanol (total of 144 kg) was charged and distilled in vacuo (30 L distilled) until the required removal of the previous solvents was achieved (toluene <15 mg/ml, cyclohexene, 0.05 mg/ml). The batch (11.69 kg of enone in 136.2 kg of solution) was held for further reaction in Example 4.

(Because t-Butanol freezes at 26° C., all drums of pure solvent and batch solutions were stored on a heating pad to maintain a temperature of ca 40° C.)

| HPLC Conditions | |
|---|---|
| Column | Zorbax SB Phenyl 250 × 4.6 mm I.D. |
| Eluent A | ACN |
| Eluent B | Aqueous 0.1 v/v % $H_3PO_4$ |
| Gradient | 30% A to 80% A in 25 min; hold for 5 min |
| Flow | 1.5 ml/min |
| Inj vol | 20 µl |
| Detection | UV at 192 nm (benzene, cyclohexene), 245 nm (enone), 295 nm (dienone) |
| Column temp | 35° C. |
| Sample preparation | 100x–1000x dilution with acetonitrile; waste aq layers diluted 10x–25x (non-linearity for dienedione, enone) |

| Compound | Retention Times |
|---|---|
| Benzene | 7.7 |
| Toluene | 10.0 |
| Cyclohexene | 10.9 |
| Dienedione | 13.9 |
| Enone | 14.9 |

EXAMPLE 4
Preparation of Seco acid (5)

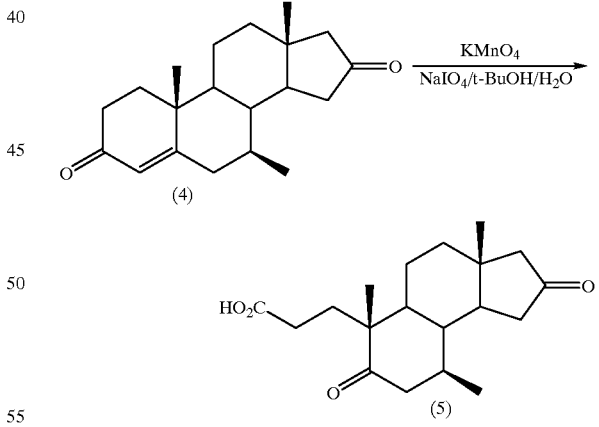

Enone (4) (11.69 assay kg) was converted to seco acid (10.3 assay kg) in 83% yield in two batches. The product was not isolated but held as a solution in ethyl acetate for Example 5.

The oxidizing solution was made up first. Water (150 L), sodium periodate (25.54 kg) and potassium permanganate (0.47 kg) were added to the reaction vessel and the mixture warmed to 65° C. until all the solids had dissolved (ca 30 minutes).

A solution of enone (4) (5.9 kg) in t-butanol (70 kg) was added to a second reaction vessel and rinsed in with t-butanol (16 kg). A solution of sodium carbonate (2.10 kg) in water (80 L) was added to the enone solution and stirred at 55° C. The oxidant was added over 1 hr, maintaining the temperature at 60° C.

The batch was aged at 60° C. for 30 mins then sampled and assayed for starting material (0.07 mg/ml, 99% complete), and then heated at 80° C. for 30 mins to decompose excess oxidant. The resulting brown slurry was cooled to 12–15° C., aged for 15 mins then filtered through a 65 cm filter fitted with a polypropylene cloth. The vessel and filter pad were rinsed with aqueous t-butanol (water 70 L, t-butanol 35 L). The filter removed the bulk of the inorganic solids but some fine brown material passed through.

The liquors were returned to the reaction vessel via a 0.5µ cotton cartridge filter, then the pH of the solution was measured at 9. The cartridge filter became blocked with the fine brown inorganic solid and required changing several times during the transfer. If the pH had been <9, it would have been adjusted by addition of sodium carbonate solution.

Hexane (30 kg) was added. The mixture was agitated for 15 minutes, settled for 15 mins then the aqueous layer cut to drums and the hexane layer cut to waste. The aqueous phase was returned to the reaction vessel together with ethyl acetate (41 kg), then the pH of the batch adjusted to 1–2 by addition of 12 N hydrochloric acid solution, maintaining the temperature at 15–20° C. The mixture was stirred for 15 mins, settled for 30 mins and both phases cut to plastic lined drums. The aqueous phase was returned to the vessel and extracted with ethyl acetate (26 kg). This extraction was repeated, and then all the organic phases combined in the reaction vessel, and washed with 10% brine solution (27 L). The aqueous phase was cut to waste and the organic phase drummed and assayed.

| HPLC Conditions | |
| --- | --- |
| Column | Zorbax SB Phenyl 250 × 4.6 mm I.D. |
| Eluent A | ACN |
| Eluent B | Aqueous 0.1 v/v % $H_3PO_4$ |
| Gradient | 30% A to 80% A in 25 min; hold for 7 min |
| Flow | 1.5 ml/min |
| Inj vol | 20 µl |
| Detection | UV at 192 nm (seco acid), 245 nm (enone) |
| Column temp | 35° C. |
| Sample preparation | 100x dilution with acetonitrile; waste aq, hexane layers diluted 10x–25x |

| Compound | Retention Times |
| --- | --- |
| Acetic acid | 2.1 |
| Ethyl acetate | 3.6 |
| Seco acid | 8.1 |
| Toluene | 10.0 |
| Enone | 14.9 |

EXAMPLE 5

Preparation of Enelactam Ketone (6)

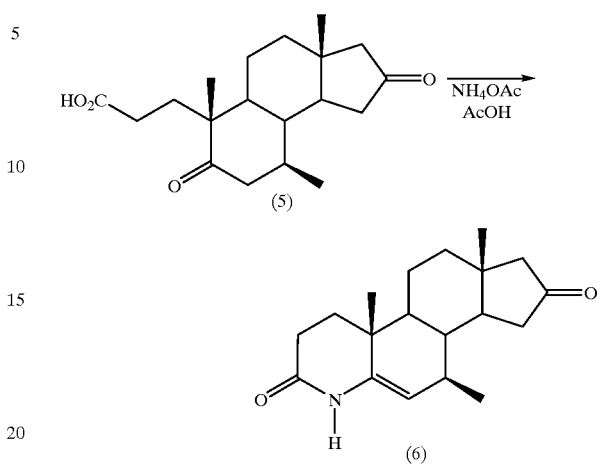

Seco-acid (9.8 kg) was converted to ene lactam ketone (9.07 kg) in a single batch. The product was not isolated, but instead carried through to Example 6 as a toluene solution.

A solution of seco-acid (10.3 kg) in ethyl acetate (282 kg) was added to a reaction vessel and concentrated in vacuo to a minimum stirred volume of ca 35 L. The solvent was then switched to acetic acid in vacuo. A total of 80 kg of acetic acid was added, and 60 L distilled to achieve an ethyl acetate concentration of <1 mg/ml in a final volume of 76 L (seco-acid concentration: 124.9 g/L). A portion of this solution (4 L, containing 500 g of seco-acid) was removed for other studies.

The remaining solution (9.8 kg in 72 L) was diluted with acetic acid to a total volume of 150 L then BHT (0.1 kg) and ammonium acetate (23.7 kg) were added via the charge port and the mixture warmed to reflux. Acetic acid (60 L) was distilled and then reflux continued for a total of 5 hrs. The progress of the reaction was monitored by HPLC and the reaction was considered complete when the concentration of seco-acid fell to <0.5 mg/ml.

The batch was cooled to 20° C., then toluene (100 L) and water (100 L) added, the solution stirred for 20 mins, settled for 20 mins and both phases cut to plastic lined drums. The aqueous phase was returned to the reaction vessel and extracted with toluene (50 L). The organic phases were combined, washed with 5% aqueous sodium chloride solution (50 L) and assayed (total volume 160 L, 56.7 g/L for 98.5% yield). The solution was concentrated in vacuo to give a thick slurry (37 L) of ene-lactam ketone.

| HPLC Conditions | |
| --- | --- |
| Column | Zorbax SB Phenyl 250 × 4.6 mm I.D. |
| Eluent A | ACN |
| Eluent B | Aqueous 0.1 v/v % $H_3PO_4$ |
| Gradient | 30% A to 80% A in 20 min; hold for 15 min |
| Flow | 1.5 ml/min |
| Inj vol | 20 µl |
| Detection | UV at 192 nm (seco acid), 240 nm (enelactam) |
| Column temp | 35° C. |
| Sample preparation | 100x dilution with acetonitrile; waste aq layers diluted 25x |

-continued

| Compound | Retention Times |
|---|---|
| Acetic acid | 2.1 |
| Ethyl acetate | 3.5 |
| Seco acid | 8.5 |
| Toluene | 9.4 |
| Enelactam ketone | 9.9 |
| BHT | 17.1 |

EXAMPLE 6
Preparation of Enelactam Alcohol (7)

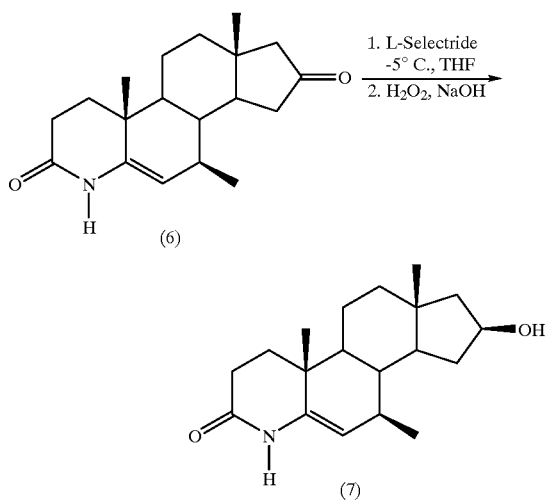

The slurry of ene-lactam ketone (9.07 kg) in toluene (35 L) in the reaction vessel was diluted with THF (89 kg) and cooled to −5° C. L-Selectride® (34.5 kg of 1M solution) was added to the slurry over 1 hr, maintaining the temperature between −5° C. and 0° C. The batch was aged at 0° C. for 20 mins then sampled. HPLC analysis showed that 11.7 mol % still remained. Further L-Selectride® (3.4 kg) was added then aged for 40 minutes at 0° C. and sampled. HPLC analysis showed that 9.9 mol % still remained.

The reaction was quenched by addition of 20% aqueous sodium hydroxide solution (37.4 kg), maintaining the temperature at <20° C., followed by 27% hydrogen peroxide (19.8 kg) at <30° C. The mixture was stirred at 15–20° C. for 1 hr then excess peroxide confirmed using a Merekoquant test strip (E. Merck).

The nitrogen purge rate was increased to 15 L/min during the hydrogen peroxide addition.

10% aqueous sodium sulfite solution (129 kg) was added, and the batch aged for 15 mins. The absence of peroxide was confirmed, and then the batch was settled for 15 mins and the aqueous phase cut to waste. 10% aqueous sodium chloride solution (58 kg) was added, the mixture agitated for 5 mins, settled for 15 mins and the aqueous phase cut to waste. The brine wash was repeated.

The organic phase (128.3 kg) was transferred to another reaction vessel via a 0.5μ cotton cartridge filter. The batch was concentrated to ca 40 L at atmospheric pressure then the solvent was switched to acetonitrile. A total of 200 kg of acetonitrile was charged and the mixture distilled to a final volume of 65 L. A sample was taken and toluene level (spec-200 mg/ml, measured-0.7 mg/ml) and KF(spec-400 mg/L, measured-73 mg/L) measured.

The batch was allowed to cool to room temperature slowly overnight with gentle agitation, and then cooled to 5° C. over 1 hr and aged for 30 minutes. The solid was collected on a 33 cm stainless steel filter, washed with acetonitrile, then dried at ambient temperature in vacuo overnight. The dry solid was bagged.

| HPLC Conditions: | |
|---|---|
| Column | Zorbax SB Phenyl 250 × 4.6 mm I.D. |
| Eluent A | ACN |
| Eluent B | Aqueous 0.1 v/v % $H_3PO_4$ |
| Gradient | 30% A to 80% A in 20 min; hold for 15 min |
| Flow | 1.5 ml/min |
| Inj vol | 20 μl |
| Detection | UV at 240 nm (enelactam ketone, enelactam alcohol) and 200 nm (BHT, toluene) |
| Column temp | 35° C. |
| Sample preparation | 100x dilution with acetonitrile; waste aq layers, filtrate and washes diluted 25x |

| Compound | Retention Times |
|---|---|
| Enelactam 16-β alcohol | 8.7 |
| Toluene | 9.5 |
| Enelactam ketone | 9.9 |
| BHT | 17.1 |

EXAMPLE 7
Preparation of Lactam Alcohol (8)

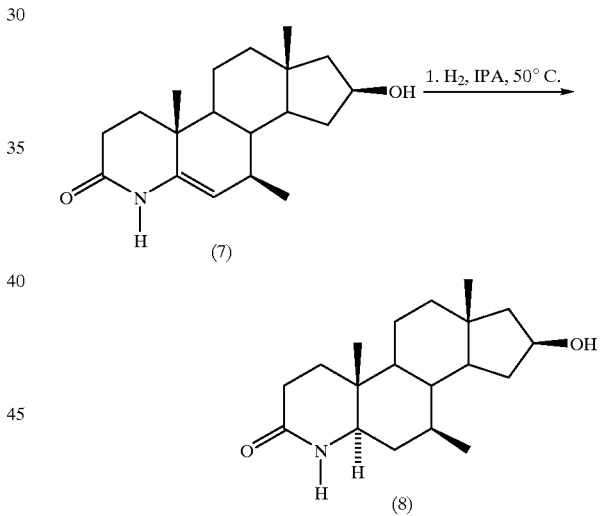

Ene-lactam alcohol (750 g) was dissolved in a mixture of IPA (10 L) and water (1.6 L) by warming to 30–40° C. in a 20 L flask. BHT (3 g) and 50% wet 10% Pd/C (375 g) was added and the mixture charged using vacuum via the dip-leg to a 20 L autoclave, and then rinsed in with IPA (1 L). The slurry was stirred under an atmosphere of hydrogen (60 psig) at 50° C. for 6 hours then at 68° C. for 16 hrs. The batch was sampled via the dip-leg and checked for completion by HPLC (spec<0.05 A % starting material). If the end point had not been reached, stirring under hydrogen was continued.

The hydrogenation was carried out at 50° C. for the first few half-lives and then warmed to 68° C. Meeting the end of reaction specification is important as ene-lactam alcohol is carried through to the final product.

The batch was cooled to 30–40° C., flushed with nitrogen several times, then transferred from the autoclave and filtered through Solka Floc diatomaceous earth (1 kg). The autoclave and filter pad were washed with 1:10 water/IPA (2 L), and the combined filtrates stored.

The procedure above was repeated 10 times and the 10 batches of filtrate were combined and concentrated at atmospheric pressure to a volume of ca 25 L. After cooling to room temperature, water (42 L) was added over 45 minutes and the batch cooled to 5° C.and aged for 1 hr. The solid was collected on a 33 cm filter fitted with a polypropylene cloth and then washed with 4:1 water/IPA (10 L). The damp solid was transferred to trays and dried in vacuo at 35° C. overnight to give the lactam alcohol (8).

EXAMPLE 8

Preparation of 7β-Methyl-16α-hydroxy-4-aza-5α-androstan-3-one (10a)

To a suspension of 7β-methyl 16β-hydroxy-4-aza-5α-androstan-3-one (8) (98.0 g, 0.321 moles) in toluene (2.5 L) was added triphenylphosphine (168.4 g, 0.642 moles), 4-nitrobenzoic acid (107.3 g, 0.642 moles), diethyl azodicarboxylate (107.3 ml, 0.642 moles). The mixture was heated at 80° for 1.5 hr with mechanical stirring in a $N_2$ atmosphere. The toluene was removed in vacuo; the residue dissolved in $CH_2Cl_2$ and washed once with 1 N HCl and saturated brine. The aqueous washes were extracted once with $CH_2Cl_2$. The combined $CH_2Cl_2$ extracts were dried ($MgSO_4$) and concentrated in vacuo. The residue was partially purified by column chromatography on 4 Kg of silica gel eluting with 5–25% acetone-$CH_2Cl_2$ to give a mixture of the desired 16β-(4-nitrophenyl) ester (9a) and triphenylphosine oxide.

The impure 4-nitrophenyl ester was suspended in EtOH (6.8 L) and 0.5 N NaOH (1.3 L, 0.65 moles) was added. The mixture was stirred mechanically at room temperature for 1.5 hr in a $N_2$ atmosphere. Most of the EtOH was removed in vacuo The residue was diluted with $H_2O$ and extracted three times with $CH_2Cl_2$. The combined $CH_2Cl_2$ extracts were washed once with 1N HCl and saturated brine. The aqueous washes were extracted twice with $CH_2Cl_2$. The combined $CH_2Cl_2$ extracts were dried ($MgSO_4$) and (Concentrated in vacuo. The residue as stirred with 20% acetone-$CH_2Cl_2$ (500 ml) for 18 hr, filtered, and dried to give the title compound. Additional product was obtained from column chromatography (silica gel, elution with 20–40% acetone-$CH_2Cl_2$ and 5–10 MeOH—$CH_2Cl_2$) of the residue from the 20% acetone-$CH_2Cl_2$ extracts.

500 MHz $^1$H NMR (CDCl$_3$): δ 0.76 (s, 3H); 0.88 (s, 3H); 1.03 (d, 3H); 3.12 (dd, 1H); 4.46 (m, 1H); 5.73 (bs, 1H).

EXAMPLE 9

Preparation of 7β-Methyl-16α-hydroxy-4-aza-5α-androst-1-en-3-one (11a)

7β-Methyl-16β-hydroxy-4-aza-5α-androstan-3-one (10a) (83.8 g, 0.274 moles) was suspended in toluene (2 L), and about 300 ml was distilled at atmospheric pressure. To the cooled suspension was added bis(trimethylsilyl) trifluoroacetamide (340 g, 1.32 moles), 2,3-dichloro-5,6-dicyano-1,4-benzoquinone (71.5 g, 1.15 moles) and trifluoromethylsulfonic acid (1.9 ml, 0.021 moles). The dark mixture was stirred at room temperature for 18 hrs. Methyl acetoacetate (3.5 ml, 0.032 moles) was added, and the mixture was heated under reflux for 19 hrs. TLC (1:1 acetone-$CH_2Cl_2$) indicated that (10a) was still present. Bis (trimethylsilyl)trifluoroacetamide (95.9 g, 0.373 moles), 2,3-dichloro-5,6-dicyano-1,4-benzoquinone (12.5 g, 0.55 moles) and trifluoromethylsulfonic acid (1.0 ml) were added, and the mixture heated at reflux for 19 hrs. The cooled reaction was extracted with a mixture of saturated NaHCO$_3$ (1 L), water (1 L), and sodium sulfite (50 g). The organic phase was washed once with saturated NaHCO$_3$ and saturated NaCl solutions. The combined aqueous phases were extracted twice with $CH_2Cl_2$. The combined organic phases were evaporated in vacuo without drying. The residue was dissolved in $CH_2Cl_2$ (1 L) and stirred at room temperature for 1.25 hr with 2N HCl (1 L). The acid phase was extracted three times with $CH_2Cl_2$. The combined $CH_2Cl_2$ phases were evaporated in vacuo to give crude (11). The material was purified by column chromatography on silica gel (1.6 Kg). The steroid was dissolved in a small amount of MeOH—$CH_2Cl_2$ for loading on the column; then elution with 5–40% acetone-$CH_2Cl_2$ and 5–10% MeOH—$CH_2Cl_2$ gave after evaporation in vacuo and flushing with hexane the title compound as a brown solid.

500 MHz $^1$H NMR (CDCl$_3$): δ 0.75 (s, 3H); 0.92 (s, 3H); 1.02 (d, 3H); 3.36 (dd, 1H); 4.44 (m, 1H); 5.30 (bs, 1H), 5.81 (dd, 1H); 6.81 (d, 1H).

EXAMPLE 10

Preparation of 7β-Methyl-16α-methanesulfonyloxy-4-aza-5α-androst-1-en-3-one (12a)

A magnetically stirred suspension of 7β-methyl-16α-hydroxy-4-aza-5α-androst-1-en-3-one (11a) (73.8 g, 0.244 moles), pyridine (52 ml, 0.641 moles), and 4-dimethylaminopyridine (2.98 g, 0.0244 moles) in $CH_2Cl_2$ (1 L) was cooled to 0–5° while methanesulfonyl chloride (47.2 ml, 0.61 mole) was added dropwise over 15 min. After 20 min the ice bath was removed, and the mixture was stirred at room temperature for 18 hrs. TLC (30% acetone-$CH_2Cl_2$) indicated a little 11a was still present; small quantities (10% of initial amounts) of pyridine, DMAP, and MsCl were added. After 2.5 hr at room temperature no 11a was detectable by TLC. The reaction mixture was washed with water (2 L), and the aqueous wash back extracted with $CH_2Cl_2$. The combined $CH_2Cl_2$ phases were washed with 1N HCl (1 L), and the acid wash was back extracted with $CH_2Cl_2$. The combined $CH_2Cl_2$ phases were washed once with water, saturated NaHCO$_3$, and saturated NaCl and dried ($MgSO_4$). Evaporation in vacuo gave crude 12a. The material was purified by column chromatography on silica gel (1.6 Kg). Elution with 10–30% acetone-$CH_2Cl_2$ and evaporation in vacuo gave the pure material which was recrystallized from $CH_2Cl_2$-hexane to give the title compound as a tan solid.

500 MHz $^1$H NMR (CDCl$_3$): δ 0.77 (s, 3H); 0.93 (s, 3H); 1.02 (d, 3H); 2.99 (s, 3H); 3.38 (dd, 1H); 5.20 (m, 1H); 5.30 (bs, 1H), 5.82 (dd, 1H); 6.80 (d, 1H).

EXAMPLE 11

Preparation of 7β-Methyl-16β-(4-(methylsulfonyl) phenoxy)-4-aza-5α-androst-1-en-3-one (13a)

A magnetically stirred suspension of 7β-methyl-16α-methanesulfonyloxy-4-aza-5α-androst-1-en-3-one (12a) (1.14 g, 3 mmoles), 4-(methylsulfonyl)phenol (Acros) (0.542 g, 3.15 mmoles), and cesium carbonate (1.47 g, 4.5 mmoles) in DMSO (6 ml) was heated at 65° for 6 hours in a $N_2$ atmosphere. The cooled suspension was diluted with water (60 ml), and the suspension stirred at room temperature for 30 min. The cream colored solid was filtered, slurry-washed three times with water, and dried (house vacuum, 45°, 16 hrs) to give crude 13a. HPLC purity: 87.8% (YMC J'sphere ODS-H80 column, 250×4.6 mm, 70/30 MeCN/0.1% TFA (10 min), then to 90/10 over 5 min, 1.0 ml/min, PDA detection at 200 nm, 13 retention time=6.68 min). Recrystallization from MeCN (35 ml) gave 13, mp 245–247°. HPLC purity 98.7% (one impurity, 1.05%, 6.18 min).

500 MHz $^1$H NMR (CDCl$_3$): δ 0.96 (s, 3H); 0.99 (s, 3H); 1.06 (d, 3H); 3.04 (s, 3H); 3.38 (m, 1H); 4.82 (m, 1H); 5.19 (bs, 1H), 5.84 (dd, 1H); 6.81 (d, 1H); 6.95 (d, 2H); 7.85 (d, 2H).

A larger batch of 13 was prepared using less pure 12. On a 20 mmoles scale 12a was reacted as above to give crude 13a. Chromatography on silica gel with EtOAc, followed by recrystallization from MeOH afforded pure 13a (HPLC purity: 99.3%). Recrystallization from MeOH (charcoal) gave 13a in two crops (Crop 1 purity: 99.5%) and (Crop 2 purity: 99.6%), mp 245–247°.

EXAMPLE 12

Preparation of 7β-methyl-16β-[2-(5-phenyl)pyrazinyloxy]-4-aza-5α-androst-1-en-3-one (14)

To a solution of 7β-methyl-16α-methanesulfonyloxy-4-aza-5α-androst-1-en-3-one (30 mg, 0.079 mmoles) in dimethylsulfoxide (150 μL) in a N$_2$ atmosphere was added 2-hydroxy-5-phenylpyrazine (19.2 mg, 0.095 mmoles) [S. Sugiura et al, *Yakugahu Zasshi* 1969, 89, 1646–1651] and cesium carbonate (41 mg, 0.126 mmoles) and the mixture stirred at 60° C. for 18 hours. The cooled reaction mixture was diluted with water, and the resulting precipitate filtered, washed with water and dried. Preparative thin layer chromatography on silica gel plates eluting with 4:1 methylene chloride:acetone provided the title compound as a white solid. NMR (CDCl$_3$): δ 0.97 (s, 3H); 1.04 (s, 3H); 1.07 (d, 3H); 3.39 (dd, 1H); 5.29 (s, 1H); 5.40 (m, 1H); 5.84 (dd, 1H); 6.83 (d, 1H); 7.39–7.50 (m, 3H); 7.92 (d, 2H); 8.25 (s, 1H); 8.51 (s, 1H); m/e (EI)=457.

The following compounds were prepared in a similar manner:

15. 7β-methyl-16β-[2-(5-(4-tolyl)pyrazinyloxy)]-4-aza-5α-androst-1-en-3-one. m/e, electrospray ionization, m+1=472.
16. 7β-methyl-16β-[2-(5-(4-methoxyphenyl)pyrazinyloxy)]-4-aza-5α-androst-1-en-3-one. m/e, electrospray ionization, m+1=488.
17. 7β-methyl-16β-[2-(5-(4-(methanesulfonyl)phenyl)pyrazyloxy)]-4-aza-5α-androst-1-en-3-one. m/e, electrospray ionization, m+1=536.
18. 7β-methyl-16β-[2-(5-(3,4-dimethoxyphenyl)-pyrazyloxy)]-4-aza-5α-androst-1-en-3-one. m/e, electrospray ionization, m+1=518.
19. 7β-methyl-16β-[2-(6-methyl)pyridyloxy]-4-aza-5α-androst-1-en-3-one. NMR (CDCl$_3$): δ 0.95 (s, 3H); 1.00 (s, 3H); 1.05 (d, 3H); 2.47 (s, 3H); 3.38 (dd, 1H); 5.29 (m, 1H); 5.52 (bs, 1H); 5.81 (dd, 1H); 6.47 (d, 1H); 6.68 (d, 1H); 6.78 (d, 1H); 7.45 (m, 1H).
20. 7β-methyl-16β-[2-(4-methyl)pyridyloxy]-4-aza-5α-androst-1-en-3-one. NMR (CDCl$_3$): δ 0.94 (s, 3H); 0.98 (s, 3H); 1.03 (d, 3H); 2.31 (s, 3H); 3.36 (dd, 1H); 5.36 (m, 1H); 5.54 (bs, 1H); 5.81 (dd, 1H); 6.52 (d, 1H); 6.69 (d, 1H); 6.78 (d, 1H); 8.00 (d, 1H).
21. 7β-methyl-16β-[3-(6-methyl)pyridyloxy]-4-aza-5α-androst-1-en-3-one. m/e, (EI)=394.
22. 7β-methyl-16β-[3-(5-chloro)pyridyloxy]-4-aza-5α-androst-1-en-3-one. m/e, (EI)=414.
23. 7β-methyl-16β-[3-(5-methyl)pyidyloxy]-4-aza-5α-androst-1-en-3-one. NMR (CDCl$_3$): δ 0.94 (s, 3H); 0.98 (s, 3H); 1.05 (d, 3H); 2.39 (s, 3H); 3.38 (dd, 1H); 4.76 (m, 1H); 5.41 (bs, 1H); 5.81 (dd, 1H); 6.79 (d, 1H); 7.16 (s, 1H); 8.04 (s, 2H).
24. 7β-methyl-16β-[3-(6-acetylamino)pyridyloxy]-4-aza-5α-androst-1-en-3-one. m/e, electrospray ionization, m+1=438.
25. 7β-methyl-16β-[3-(6-(4-fluoro)phenyl)pyridyloxy]-4-aza-5α-androst-1-en-3-one. NMR (CDCl$_3$): δ 0.95 (s, 3H); 1.00 (s, 3H); 1.05 (d, 3H); 3.37 (dd, 1H); 4.83 (m, 1H); 5.39 (bs, 1H); 5.80 (dd, 1H); 6.79 (d, 1H); 7.14 (t, 2H); 7.30 (m, 1H); 7.62 (d, 1H); 7.91 (dd, 2H); 8.30 (d, 1H).
26. 7β-methyl-16β-[4-(2,6-dimethyl)pyridyloxy]-4-aza-5α-androst-1-en-3-one. NMR (CDCl$_3$): δ 0.95 (s, 3H); 0.97 (s, 3H); 1.06 (d, 3H); 2.54 (s, 6H); 3.38 (dd, 1H); 4.78 (m, 1H); 5.59 (bs. 1H); 5.81 (dd, 1H); 6.45 (s, 2H); 6.77 (d, 1H).
27. 7β-methyl-16β-[4-(6-phenyl)pyrimidyloxy]-4-aza-5α-androst-1-en-3-one. m/e, electrospray ionization, m+1=458.
28. 7β-methyl-16β-[2-(6-phenyl)pyrimidyloxy]-4-aza-5α-androst-1-en-3-one. m/e, electrospray ionization, m+1=458.
29. 7β-methyl-16β-[2-(5,6-diphenyl)1,3,4-triazinyloxy]-4-aza-5α-androst-1-en-3-one. m/e, electrospray ionization, m+1=535.
30. 7β-Methyl-[16β-(2-quinolyloxy)]-4-aza-5α-androst-1-en-3-one. m/e, electrospray ionization, m+1=431
31. 7β-Methyl-[16β-(3-isoquinolyloxy)]-4-aza-5α-androst-1-en-3-one. m/e, electrospray ionization, m+1=431.
32. 7β-Methyl-[16β-(1-isoquinolyloxy)]-4-aza-5α-androst-1-en-3-one. m/e, electrospray ionization, m+1=431
33. 7β-methyl-16β-(2-(4-methylsulfony)pyrimidyloxy)-4-aza-5α-androst-1-en-3-one. m/e, electrospray ionization, m+1=460
34. 7β-methyl-16β-(3-isoxazolyloxy)-4-aza-5α-androst-1-en-3-one. NMR (CDCl$_3$): δ 0.94 (s, 3H); 0.99 (s, 3H); 1.04 (d, 3H); 3.38 (dd, 1H); 5.05 (m, 1H); 5.74 (bs, 1H); 5.82 (dd, 1H); 5.90) (d, 1H); 6.80 (d, 1H); 8.09 (d, 1H).
35. 7β-methyl-16β-(5-(1-methyl-3-trifluoromethyl)-1H-pyrazolyloxy)-4-aza-5α-androst-1-en-3-one. NMR (CDCl$_3$): δ 0.92 (s, 3H); 0.96 (s, 3H); 1.04 (d, 3H); 3.34 (dd, 1H); 3.65 (s, 3H); 4.69 (q, 1H); 5.58 (bs, 1H); 5.67 (s, 1H); 5.81 (d, 1H); 6.79 (d, 1H).
36. 7β-methyl-16β-(3-(1-methyl-5-trifluoromethyl)-1H-pyrazolyloxy)-4-aza-5α-androst-1-en-3-one. NMR (CDCl$_3$): δ 0.92 (s, 3H); 0.96 (s, 3H); 1.04 (d, 3H); 3.34 (dd, 1H); 4.73 (q, 1H); 5.87 (bs, 1H); 5.79 (d, 1H); 6.79 (d, 1H); 7.09 (m, 1H); 7.18 (t, 1H); 8.16 (d, 1H); 8.21 (s, 1H).

EXAMPLE 13

Preparation of 7β-methyl-16β-(2-pyrimidyloxy)-4-aza-5α-androst-1-en-3-one (41)

To a suspension of KH (35% oil dispersion, 95 mg, 0.825 mmoles) in DMF (2 ml) was added 7β-methyl-16β-hydroxy-4-aza-5α-androst-1-en-3-one (30 mg, 0.079 mmoles). The mixture was stirred at room temperature for 30 min in a N$_2$ atmosphere; 2-chloropyrimidine (200 mg, 1.65 mmoles) was added and stirring was continued for 3 days. The reaction mixture was diluted carefully with water, and the resulting precipitate filtered, washed with water and dried. Column chromatography on silica gel with 15%:acetone-methylene chloride provided the title compound as a white solid. NMR (CD$_3$OD): δ 0.93 (s, 3H); 1.03 (s, 3H); 1.06 (d, 3H); 3.30 (dd, 1H); 5.40 (m, 1H); 5.75 (s, 1H); 6.96 (d, 1H); 7.05 (t, 1H); 8.53 (d, 2H). m/e, electrospray ionization, m+1=382.

The following examples were prepared in a similar manner:

37. 7β-methyl-16β-(2-pyridyloxy)-4-aza-5α-androst-1-en-3-one. m/e, electrospray ionization, m+1=381.
38. 7β-methyl-16β-[2-(5-carbonylamino)pyridyloxy]-4-aza-5α-androst-1-en-3-one. m/e, electrospray ionization, m+1=424
39. 7β-methyl-16β-(3-pyridyloxy)-4-aza-5α-androst-1-en-3-one. NMR (CDCl$_3$): δ 0.92 (s, 3H); 0.96 (s, 3H); 1.04

(d, 3H); 3.34 (dd, 1H); 4.73 (q, 1H); 5.87 (bs, 1H); 5.79 (d, 1H); 6.79 (d, 1H); 7.09 (m, 1H); 7.18 (t, 1H); 8.16 (d, 1H); 8.21 (s, 1H).

40. 7β-methyl-16β-(4-pyridyloxy)-4-aza-5α-androst-1-en-3-one. m/e, electrospray ionization, m+1=381.

42. 7β-methyl-16β-(2-(4-phenyl)pyrimidyloxy)-4-aza-5α-androst-1-en-3-one. m/e, electrospray ionization, m+1=458.

43. 7β-methyl-16β-[2-(6-chloro)pyrazinyloxy]-4-aza-5α-androst-1-en-3-one. NMR (CDCl₃): δ 0.92 (s, 3H); 0.96 (s, 3H); 1.02 (d, 3H3.34 (dd, 1H); 5.27 (bs, 1H); 5.34 (q, 1H); 5.80 (d, 1H); 6.78 (d, 1H); 8.05 (s, 1H); 8.08 (s, 1H).

44. 7β-methyl-16β-[2-(3,6-dimethylpyrazinyloxy)]-4-aza-5α-androst-1-en-3-one. NMR (CDCl₃): δ 0.92 (s, 3H); 0.98 (s, 3H); 1.02 (d, 3H); 2.35 (s, 3H); 2.37 (s, 3H); 3.35 (dd, 1H); 5.27 (bs, 1H); 5.39 (q, 1H); 5.80 (d, 1H); 6.79 (d, 1H); 7.78 (s, 2H).

45. 7β-methyl-16β-(2-(6-chloro)pyridazinyloxy)-4-aza-5α-androst-1-en-3-one. NMR (CDCl₃): δ 0.92 (s, 3H); 0.95 (s, 3H); 1.01 (d, 3H); 3.34 (dd, 1H); 5.25 (bs, 1H); 5.52 (q, 1H); 5.79 (d, 1H); 6.79 (d, 1H); 6.88 (d, 1H); 7.32 (d, 1H). Mass spectrum: m/e 416 (M+1).

46. 7β-methyl-16β-[3-(6-phenyl)pyridazinyloxy]-4-aza-5α-androst-1-en-3-one. NMR (CDCl₃): δ 0.92 (s, 3H); 0.99 (s, 3H); 1.04 (d, 3H); 3.34 (dd, 1H); 5.27 (bs, 1H); 5.64 (q, 1H); 5.80 (d, 1H); 6.79 (d, 1H); 6.98 (d, 1H); 7.45 (m, 3H); 7.75 (d, 1H); 7.98 (d, 2H). Mass spectrum: m/e 458 (M+1).

47. 7β-methyl-16β-(2-benzoxazolyloxy)-4-aza-5α-androst-1-en-3-one. m/e, electrospray ionization, m+1=381.

48. 7β-methyl-16β-(2-benzthiazolyloxy)-4-aza-5α-androst-1-en-3-one. m/e, electrospray ionization, m+1=437.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for producing a compound of structural formula (A):

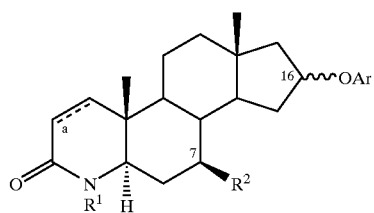

(A)

wherein:

the dotted line "a" is a single bond or double bond;

$R^1$ is H or $CH_3$;

$R^2$ is H or $CH_3$; and

Ar is an unsubstituted mono- or di-substituted phenyl, naphthyl, or 5 or 6 membered heteroaromatic ring containing at least one member selected from the group consisting of: one ring oxygen atom, one ring sulfur atom, 1–4 ring nitrogen atoms, or combinations thereof; in which the heteroaromatic ring can also be fused with one benzo or heteroaromatic ring;

produced by:

treating a compound of structural formula (B):

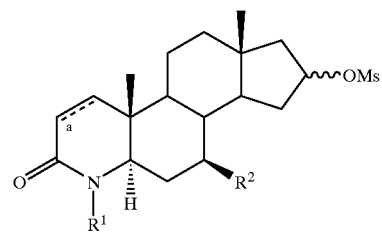

(B)

with Ar—OH and cesium carbonate in a polar aprotic solvent selected from DMSO, DM F, nitromethane, dioxane, THF, and acetonitrile, and wherein Ar is as defined above.

2. The process according to claim 1 for producing a compound of structural formula (13):

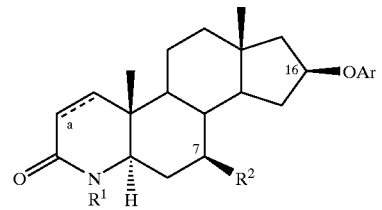

(13)

wherein:

the dotted line "a" is a single bond or double bond;

$R^1$ is H or $CH_3$;

$R^2$ is H or $CH_3$; and

Ar is an unsubstituted or mono- or di-substituted phenyl, naphthyl, or 5 or 6 membered heteroaromatic ring containing at least one member selected from the group consisting of: one ring oxygen atom, one ring sulfur atom, 1–4 ring nitrogen atoms, or combinations thereof; in which the heteroaromatic ring can also be fused with one benzo or heteroaromatic ring;

produced by:

treating a compound of structural formula (12):

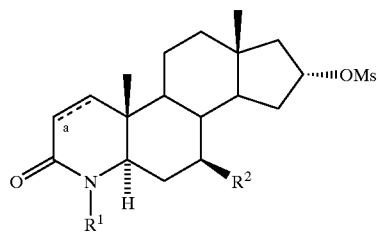

(12)

with Ar—OH and cesium carbonate in a polar aprotic solvent selected from DMSO, DMF, nitromethane, dioxane, THF, and acetonitrile, and wherein Ar is as defined above.

3. The process according to claim 2 wherein the solvent is DMSO.

4. The process according to claim 2 wherein Ar is selected from:
unsubstituted or mono- or di-substituted phenyl, naphthyl, pyridyl, furyl, pyrrolyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl, and benzoxazolyl.

5. The process according to claim 4 wherein Ar is selected from:
unsubstituted or mono- or di-substituted phenyl, naphthyl, pyridyl, pyrrolyl, pyrazinyl, pyrimidyl, and oxazolyl.

6. The process according to claim 5 wherein the dotted line "a" is a double bond;
$R^1$ is H;
$R^2$ is $CH_3$;
Ar is monosubstituted phenyl.

7. The process according to claim 6 wherein the phenyl substituent is selected from:
(1) p-methylsulfonyl;
(2) p-methyl;
(3) p-trifluoromethyl;
(4) p-chloro;
(5) p-fluoro; and
(6) p-hydroxy.

8. The process according to claim 7 wherein the phenyl substituent is p-methylsulfonyl.

* * * * *